United States Patent [19]

Buckler

[11] 4,182,856

[45] Jan. 8, 1980

[54] REAGENTS FOR USE IN BINDING ASSAYS TO DETERMINE DIPHENYLHYDANTOIN

[75] Inventor: Robert T. Buckler, Edwardsburg, Mich.

[73] Assignee: Miles Laboratories, Inc., Elkhart, Ind.

[21] Appl. No.: 899,844

[22] Filed: Apr. 25, 1978

[51] Int. Cl.$^2$ .................... C07H 17/00; C07H 17/04
[52] U.S. Cl. .......................... 536/4; 536/53; 548/314; 260/112 R; 424/12
[58] Field of Search .......................................... 536/53

[56] References Cited

U.S. PATENT DOCUMENTS

| | | | |
|---|---|---|---|
| 3,905,871 | 9/1975 | Rubenstein et al. | 195/63 |
| 4,045,556 | 8/1977 | Schwertner et al. | 260/112.5 R |
| 4,060,603 | 11/1977 | Morgan et al. | 260/112.5 R |

*Primary Examiner*—Johnnie R. Brown
*Assistant Examiner*—Blondel Hazel
*Attorney, Agent, or Firm*—Andrew L. Klawitter

[57] ABSTRACT

Reagents for use in binding assays, particularly immunoassays, to determine diphenylhydantoin and for preparing reagents employed in such assays, including β-galactosyl-umbelliferone-diphenylhydantoin conjugates, diphenylhydantoin immunogens, and $N^1$, $N^3$ and o-phenyl derivatives of diphenylhydantoin for preparing same. $N^1$ and $N^3$-ω-aminoalkyl and o-(ω-aminoalkoxy)-phenyl derivatives are prepared and coupled by amide linkage to a β-galactosyl-umbelliferone derivative to form labeled conjugates useful in homogeneous or heterogeneous binding assays. $N^1$ and $N^3$-ω-carboxyalkyl and o-(ω-carboxyalkoxy)-phenyl derivatives are prepared and coupled by amide linkage to an immunogenic polyamino acid to form immunogen conjugates against which diphenylhydantoin-specific antibodies can be raised.

5 Claims, No Drawings

REAGENTS FOR USE IN BINDING ASSAYS TO DETERMINE DIPHENYLHYDANTOIN

BACKGROUND OF THE INVENTION

1. Field of the Invention

This invention relates to novel diphenylhydantoin derivatives pertaining to binding assays for detecting diphenylhydantoin and its salt forms in liquid media, such as serum, saliva, and cerebrospinal fluid. Such derivatives include labeled diphenylhydantoin conjugates directly used in carrying out such assays. Also described are novel immunogen conjugates for preparing diphenylhydantoin-specific antibodies according to conventional techniques. Further, there are described novel intermediates useful in the synthesis of such labeled conjugates and such immunogen conjugates.

Diphenylhydantoin (5,5-diphenyl-2,4-imidazolidinedione), also known by the generic name phenytoin and by various trademarks including Dilantin, is an anticonvulsant drug useful in the management of epilepsy, having the formula:

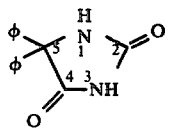

wherein
 $\phi$ represents phenyl [cf. *The Merck Index*, 9th edition, p. 952 (1976)].

Like most anti-convulsants, diphenylhydantoin possesses a low therapeutic index and has clearly separable ranges of drug concentration in blood in which it is ineffective, therapeutic, or toxic, respectively. At sufficiently high concentration, the drug is potentially toxic and is eliminated from the body at a rate which can vary within a wide range from individual to individual so that the same dose can yield an ineffective, a therapeutic, or a toxic concentration depending on the subject. Administration of usual doses of diphenylhydantoin produces serum concentrations from 5 up to 50 micrograms/milliliter ($\mu$g/ml) due to differences in the rate of hepatic metabolism of the drug. However, in almost all patients, the therapeutic range of serum concentration lies between 10 and 20 $\mu$g/ml whereas toxic signs of nystagmus, ataxia and mental changes almost invariably appear at blood levels over 20 $\mu$g/ml. With usual doses of diphenylhydantoin, some patients will have serum concentrations outside the therapeutic range, indicating the need for dosage adjustment.

2. Brief Description of the Prior Art

Over the years, many varied assay techniques have evolved for the monitoring of diphenylhydantoin levels in serum, including spectrophotometry, thin-layer chromatography, high-pressure liquid chromatography, and immunological methods. The state-of-the-art immunoassay techniques comprise the radioimmunoassay methods of Tigelaar et al, *Clin. Chim. Acta* 43:231–43:2–31–241(1973) and Cook et al as described in *Quantitative Analytic Studies in Epilepsy*, ed. Kellaway et al, Raven Press (New York, 1976), pp. 39–58; and the enzyme immunoassay technique described in U.S. Pat. Nos. 3,817,837 and 3,905,871.

A specific binding assay for detecting ligands, including drugs such as diphenylhydantoin, employing an enzyme-cleavable $\beta$-galactosyl-umbelliferone residue as label is described in pending U.S. Patent Application Ser. No. 886,094, filed Mar. 13, 1978, assigned to the instant assignee.

Methods of synthesizing diphenylhydantoin immunogen conjugates and using same to obtain specific antibodies are described by Tigelaar et al, supra and Cook et al, *Res. Commun. Chem. Pathol. and Pharmacol.* 5:767–774(1973) and in U.S. Pat. No. 3,995,021 and French Pat. No. 2,276,317.

SUMMARY OF THE INVENTION

Novel labeled diphenylhydantoin conjugates have been devised for use in binding assays having the general formula:

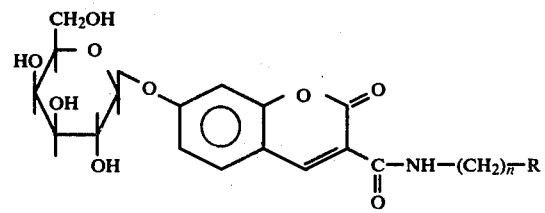

wherein
 n=2 through 6, and preferably is 4;

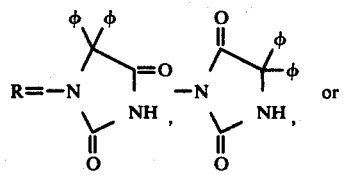

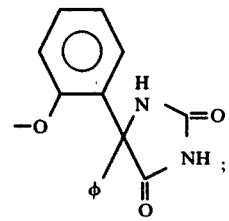

and
 $\phi$=phenyl.

These $\beta$-galactosyl-umbelliferone-diphenylhydantoin conjugates are prepared by reaction of a mixed anhydride (from $\beta$-galactosyl-umbelliferone-3-carboxylic acid and an alkyl chloroformate) with $N^1$ and $N^3$-$\omega$-aminoalkyl and o-($\omega$-aminoalkoxy)-phenyl-(comprising 2 through 6, preferably 4, methylene groups)-diphenylhydantoin derivatives.

The novel immunogen conjugates consist of the $N^1$-conjugated compound of the formula:

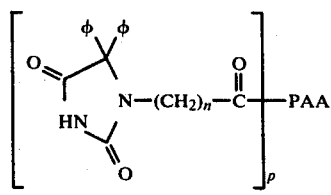

and the o-phenyl-conjugated compound of the formula:

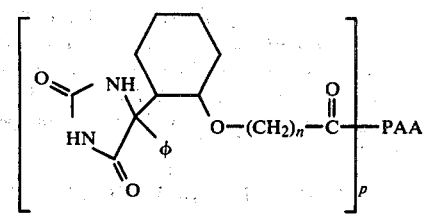

wherein, for both formulae, φ is phenyl; PAA is an immunogenic polyamino acid, preferably an albumin, bonded through an amide linkage; n=2 through 6, and preferably 4; and p=1 through 50, preferably 5 through 25. These immunogen conjugates are prepared by reaction of $N^1$ substituted ω-carboxyalkyl and o-(ω-carboxyalkoxy)-phenyl substituted (comprising 2 through 6, preferably 4, methylene groups)-diphenylhydantoin derivatives with the polyamino acid under conditions favorable to the formation of amide linkages, such as in the presence of a carbodiimide in acidic solution.

The polyamino acid may be naturally occurring or synthetic and is usually an immunogenic polypeptide or protein. The polyamino acid may comprise constituents in addition to amino acids and will usually be of molecular weight between 5,000 and 1,000,000; preferably between 15,000 and 500,000, and more usually between 30,000 and 200,000. For the most part, proteins taken from one species will be immunogenic when introduced to the blood stream of another species. Particularly useful proteins are albumins, globulins, enzymes, hemocyanins, albuminoids, glutelins, proteins having significant non-proteinaceous constituents, e.g., glycoproteins, and the like. The albumins and globulins of molecular weight between 30,000 and 200,000 are particularly preferred.

Preparation of specific antibodies using the present immunogen conjugates may follow any conventional technique. Numerous texts are available describing the fundamental aspects of inducing antibody formation, for example reference may be made to C. W. Parker, *Radioimmunoassay of Biologically Active Compounds*, Prentice-Hall (Englewood Cliffs, N.J., USA, 1976). In the usual case, a host animal such as a rabbit or goat is injected at one or more of a variety of sites with the immunogen conjugate, normally in mixture with an adjuvant. Further injections are made at the same or different site or sites at regular or irregular intervals thereafter with bleedings being taken to assess antibody titer and its rate of increase until it is determined that optimal titer has been reached. The host animal is sacrificed by exsanguination to yield a suitable volume of specific antiserum. Where desirable, purification steps may be taken to remove undesired material such as non-specific antibodies before the antiserum is considered suitable for use in performing actual assays.

1. $N^1$-Derivatives

1-I. PREPARATION OF THE LABELED CONJUGATE

The $N^1$-conjugated β-galactosyl-umbelliferone-diphenylhydantoin labeled compounds are prepared according to the reaction scheme shown in Table 1. This synthetic route is exemplified by the following method of preparing N-[4-(5,5-diphenylhydantoinyl-1)-butyl]-7-β-galactosylcoumarin-3-carboxamide (7). To follow this synthesis in Table 1, n equals 4.

5,5-Diphenyl-1-[4-(N-phthalimido)-butyl]-hydantoin (2)

Under an argon atmosphere, 2.4 g (0.05 mol) of sodium hydride (50% dispersion in mineral oil) was placed in a dry, 1 liter, 3-necked round bottom flask equipped with a mechanical stirrer and thermometer. The sodium hydride was rinsed with 250 milliliters (ml) of dry hexane. To the washed material was added a solution of 16.2 grams (g) (0.05 mol) of 3-carbethoxy-5,5-diphenylhydantoin (1) [L. Call, *Monat. Chemie 101*, 228 (1970)] in 250 ml of dry dimethylformamide (DMF). When gas evolution ceased (about 15 minutes), a solution of 15.5 g (0.055 mol) of N-(4-bromobutyl)-phthalimide was added and the reaction stirred overnight at room temperature. The resulting mixture was then combined with 5 ml of glacial acetic acid and evaporated under reduced pressure to give an oil. The oil was adsorbed onto 150 g of silica gel 60 (E. Merck Co., Darmstadt, West Germany) and used to top a column of 1000 g of silica gel 60 made up in 17:3 (v:v) toluene:ethanol. 20 ml fractions were collected.

TABLE 1

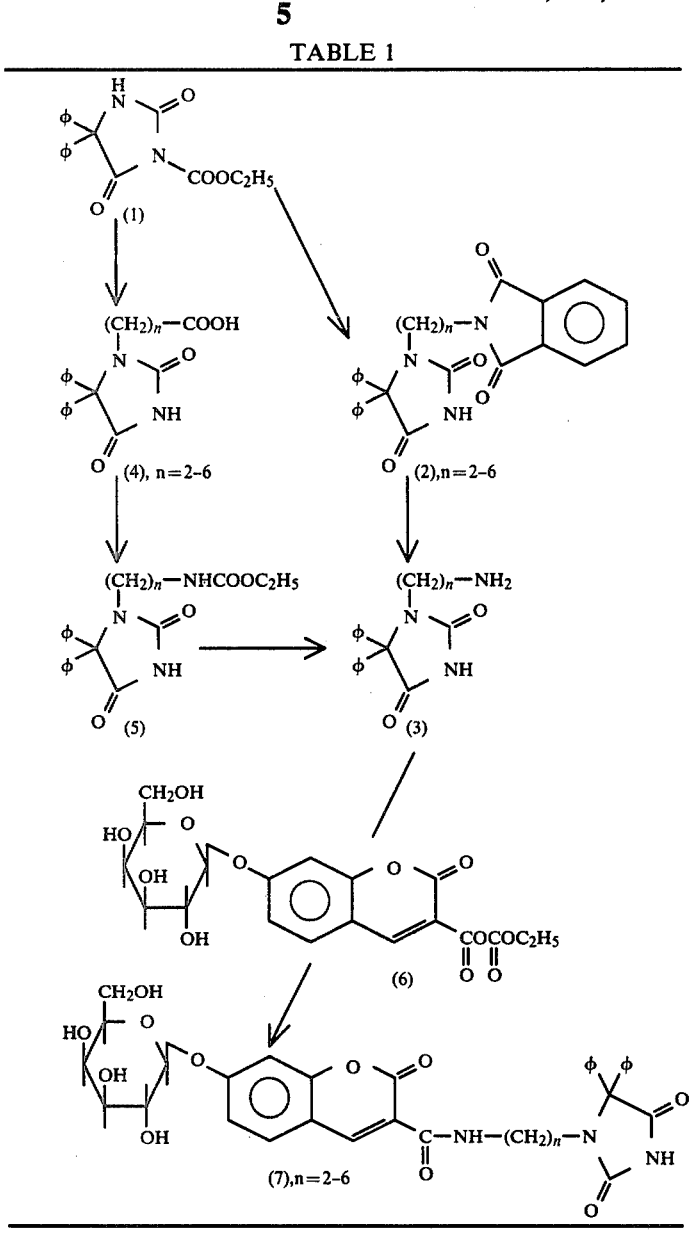

Fractions 141 to 250 were combined and evaporated. The residue was recrystallized from toluene-ethanol to give 6 g of the desired phthalimido-hydantoin (2) as fine white needles, mp 219° C.

Analysis: Calculated for $C_{27}H_{23}N_3O_4$: C, 71.51; H, 5.11; N, 9.27. Found: C, 71.67; H, 5.29; N, 8.96.

NMR Spectrum ($d_6$ DMSO): δ 0.7 (m, 2H), 1.3 (m, 2H), 3.3 (m, 4H), 7.2 (s, 10H), 7.9 (1s, 4H).

1-(4-Aminobutyl)-5,5-diphenylhydantoin (3).

A mixture of 1 g (2.2 mmole) of 5,5-diphenyl-1-[4-(N-phthalimido)-butyl]-hydantoin (2), 25 ml of absolute ethanol, and 5 ml of 88% hydrazine was refluxed under an argon atmosphere for 1 hour. After complete dissolution, a heavy white precipitate formed. When cool, the excess solvent was removed under high vacuum to leave a white solid residue. The residue was heated for 30 minutes in 100 ml of 1 N hydrochloric acid, then cooled. The insoluble material was filtered and discarded, and the filtrate neutralized with aqueous sodium bicarbonate solution. The precipitate was separated and recrystallized from pyridine to give 520 milligrams (mg) of the desired amino-hydantoin (3) as very fine white crystals, mp 254°-256° C.

Analysis: Calculated for $C_{19}H_{21}N_3O_2$: C, 70.56; H, 6.55; N, 12.99. Found: C, 70.11; H, 6.53; N, 12.90.

NMR Spectrum ($D_2O$-NaOD): δ 0.9 (m, 4H), 2.1 (m, 2H), 3.2 (m, 2H), 7.2 (s, 10H).

Alternate Preparation of 1-(4-aminobutyl)-5,5-diphenyl hydantoin (3).

Under an argon atmosphere, 4.32 g (0.09 mol) of sodium hydride (50% dispersion in mineral oil) was placed in a dry, 1 liter, 3-necked round bottom flask equipped with a mechanical stirrer and thermometer. The sodium hydride was rinsed with 250 ml of dry hexane. To the washed material was added 29 g (0.09 mol) of 3-carbethoxy-5,5-diphenylhydantoin (1) [L. Call, *Monat. Chem.* 101:228(1970)] dissolved in 250 ml of dry dimethylformamide (DMF). After stirring for one hour, hydrogen gas evolution ceased. Then 20.9 g (0.1 mol) of ethyl-5-bromovalerate was added and the reaction stirred overnight at room temperature. The DMF was removed under high vacuum and the residue partitioned between 500 ml of ether and 300 ml of water ($H_2O$). The ether phase was separated, washed with saturated sodium chloride solution, dried over anhydrous magnesium sulfate, filtered, and evaporated to give an oil. This oil was stirred at 5° C. for 3 hours in 500 ml of 2 N sodium hydroxide. Acidification with dilute hydrochloric acid precipitated an oil that was crystallized from ether and recrystallized from aqueous methanol to give 5 g of 1-(4-carboxybutyl)-5,5-diphenylhydantoin (4) as white crystals, mp 207° C.

Analysis: Calculated for $C_{20}H_{20}N_2O_4$: C, 68.17; H, 5.72; N, 7.95. Found: C, 68.14; H, 5.88; N, 7.73.

NMR Spectrum ($C_5D_5N$): δ 0.8 (m, 4H), 1.65 (t, 2H, J=8 Hz), 2.9 (t, 2H, J=8 Hz), 6.8 (m, 10H).

The mother liquors were combined and chromatographed on 1000 g of silica gel 60, eluting with 17:3 (v:v) benzene:methanol. Fractions 25 to 75 were combined, evaporated, and twice recrystallized from aqueous methanol to give an additional 2.5 g of the acid (4), mp 207° C.

A mixture of 6.4 g (0.018 mol) of 1-(4-carboxybutyl)-5,5-diphenylhydantoin (4), 50 ml of dry DMF, and 6 ml of triethylamine was cooled to 0° C. under argon while stirring. To this was added 3.2 ml (4.34 g, 0.04 mol) of ethyl chloroformate. After 1 hour at 0° C., the reaction was filtered to remove the precipitate of triethylamine hydrochloride. The filtrate was cooled to 0° C. and combined with 100 ml of DMF and 3.5 g (0.054 mol) of sodium azide in 40 ml of $H_2O$. After 2 hours at this temperature, the reaction was diluted with 2 liters of $H_2O$ and extracted with three 500 ml portions of ether. The ether extracts were combined and evaporated at 20° C. under reduced pressure. The residue amounted to 7 g of an off-white oil. The oil was taken up in 150 ml of absolute ethanol and refluxed for 2 hours. When cool, the resulting mixture was evaporated to give a clear white oil. Recrystallization from aqueous ethanol gave 1.6 g of fine crystals, mp 174° C., of 1-[4-(N-carbethoxy)-aminobutyl]-5,5-diphenylhydantoin (5).

Analysis: Calculated for $C_{22}H_{25}N_3O_4$: C, 66.81; H, 6.37; N, 10.63. Found: C, 66.20; H, 6.45; N, 10.28.

Mass Spectrum (70 eV) m/e: 395 [M+], 349 [M+ minus $OC_2H_5$], 322 [M+ minus $COOC_2H_5$], 306 [M+ minus $NHCOOC_2H_5$].

A mixture of 1.5 g (4 mmol) of 1-[4-(N-carbethoxy)-aminobutyl]-5,5-diphenylhydantoin (5) and 50 ml of 1 N sodium hydroxide was refluxed for 16 hours, then cooled and neutralized with carbon dioxide. Carbon dioxide was removed from the solution under reduced pressure and the precipitate filtered and recrystallized from dimethylsulfoxide to give 1.1 g of the aminohydantoin (3) as fine white needles, mp 254°-256° C.

Analysis: Calculated for $C_{19}H_{21}N_3O_2$: C, 70.56; H, 6.55; N, 12.99. Found: C, 69.19; H, 6.57; N, 12.23.

Mass Spectrum (70 eV) m/e: 323 [M+], 324 [MH+], 254 [$(C_6H_5)_2CHNHCH_2CH_2CH_2CH_2NH_2^+$].

N-[4-(5,5-Diphenylhydantoinyl-1)-butyl]-7-β-galactosylcoumarin-3-carboxamide (7).

The postassium salt of the β-galactoside of 3-carboxy-7-hydroxycoumarin [Burd et al, *Clin. Chem. 23*, 1402 (1977)] (808 mg, 2 mmol) was suspended in 10 ml of dry DMF and cooled to 0° C. while stirring under an argon atmosphere. To this was added 216 mg (2 mmol) of ethyl chloroformate and the reaction stirred for 3 hours to form the mixed anhydride (6). Then 969 mg (3 mmol) of 1-(4-aminobutyl)-5,5-diphenylhydantoin (3), 610 mg (5 mmol) of 4-dimethylaminopyridine, 10 ml of dry pyridine, and 10 ml of DMF were added. Stirring was continued at room temperature overnight.

To the reaction mixture was added 7 g of silica gel 60 and the solvent removed under reduced pressure. The impregnated silica gel was placed atop a column of 200 g of silica gel made up in 4:2:1 (v:v:v) n-butanol:methanol:$H_2O$. Elution was with the same solvent and 20 ml fractions were collected. Fractions 34-49 were combined and evaporated to give 550 mg of crude product which was rechromatographed on 200 g of silica gel 60 eluting with a gradient of ethyl acetate—ethanol. This gave 300 mg of an amorphous off-white solid which was taken up in 10 ml of methanol and chromatographed on a 45 cm by 3.2 cm column of Sephadex LH-20 (Pharmacia Fine Chemicals, Piscataway, New Jersey, USA) eluting with methanol. Seven ml fractions were collected. Fractions 36 to 44 were combined and evaporated to give 200 mg of a clear, faintly yellow glassy solid of the labeled conjugate (7).

Analysis: Calculated for $C_{35}H_{35}N_3O_{11}$: C, 62.40; H, 5.24; N, 6.24. Found: C, 61.74; H, 5.05; N, 6.17.

$[\alpha]_D = -35.79°$ (c 1.0, methanol).

The above-described synthesis of the $N^1$-labeled conjugate (7), n=4, can be modified to yield labeled conjugates wherein n=2 through 6 by replacing N-(4-bromobutyl)-phthalimide in the described systhesis of the phthalamido-hydantoin (2) with the appropriate N-(ω-bromoalkyl)-phthalimide as follows:

| n | alkylene |
|---|----------|
| 2 | ethylene |
| 3 | propylene |
| 5 | pentylene |
| 6 | hexylene |

1-II. PREPARATION OF THE IMMUNOGEN CONJUGATE

This synthesis is shown schematically in Table 2 and is exemplified for n=4 as follows:

26.4 mg (75 μmol) of 1-(4-carboxybutyl)-5,5-diphenylhydantoin (4) [prepared from 3-carbethoxy-5,5-diphenylhydantoin (1) as described in 1-I] was dissolved in 0.75 ml dioxane. The solution was cooled to 5° to 10° C. in an ice water bath and 17.5 μl (14.5 mg, 75 μmol) of ethyl chloroformate was added and mixed. The solution was allowed to react for 15 minutes at 5° to 10° C. before adding it to the protein solution. The protein solution was prepared by dissolving 125 mg (2.08 μmol) of bovine serum albumin (BSA, represented in Table 2 as PAA, Research Products Division of Miles Laboratories, Inc., Elkhart, Ind. USA) in 3.25 ml $H_2O$ containing 125 μl of 1 N sodium hydroxide. While vortex mixing, 3.25 ml dioxane was slowly added to the alkaline BSA solution. The BSA solution was then placed in an ice bath and the activated diphenylhydantoin derivative added. After 2 hours, the reaction mixture was brought to room temperature. 5 drops of 1 N sodium hydroxide was added to clear the cloudy solution (the pH rose to above 9).

TABLE 2

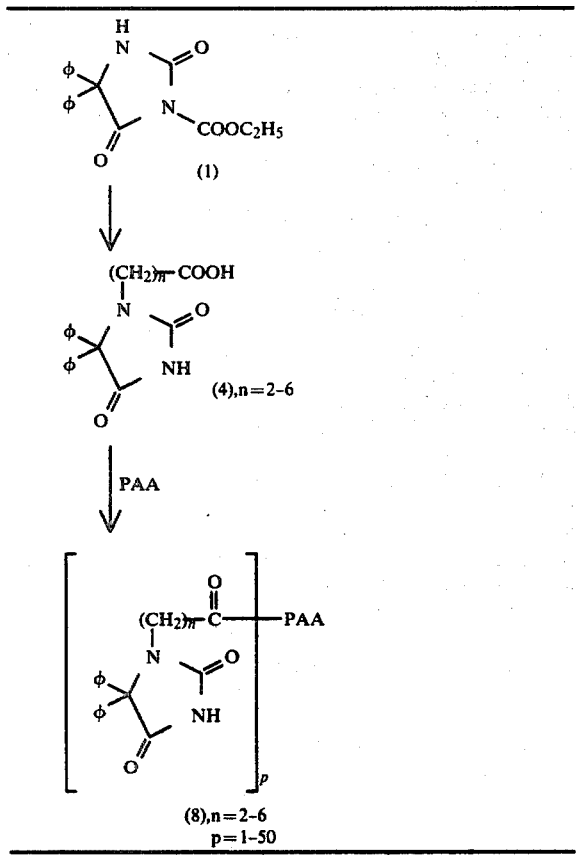

The reaction mixture was chromatographed with 50 mM ammonium formate through a 2.5×90 cm column of G-10 Sephadex. The immunogen conjugate (8) eluted in the column void volume. Spectral analysis of the product indicated 18.6 moles of diphenylhydantoin per mole of BSA.

The above-described synthesis of the N[1]-immunogen conjugate (8), n=4, can be modified to yield conjugates wherein n=2 through 6 by replacing ethyl-5-bromovalerate in the described synthesis of the acid (4) as follows:

| n | starting material |
|---|---|
| 2 | ethyl-3-bromopropionate |
| 3 | ethyl-4-bromobutyrate |
| 5 | ethyl-6-bromocaproate |
| 6 | ethyl-7-bromoheptanoate |

1-III. BINDING ASSAY FOR DIPHENYLHYDANTOIN

A. Reagents

1. Antiserum — Rabbits were immunized with the N[1]-conjugated immunogen prepared according to 1-II above.

2. Enzyme — *Escherichia coli* grade IV β-galactosidase was used (Sigma Chemical Co., St. Louis, Mo., U.S.A.). The enzyme preparation used had a specific activity of 666 units per mg of protein. One unit of activity was defined as that amount which hydrolyzed 1.0 μmol of o-nitrophenyl-β-D-galactoside per minute at pH 7.2 and 37° C.

3. Buffer — Bicine buffer [N,N-bis-(2-hydroxyethyl)-glycine, Nutritional Biochemicals Corp., Cleveland, Ohio, USA] was used at pH 8.2 and 50 mmolar at 25° C.

4. Diphenylhydantoin Standards — 25 mg of diphenylhydantoin was dissolved in 10 ml of dimethylsulfoxide (DMSO) to give a 2500 μg/ml solution. By 1:9 serial dilution with DMSO, 10 ml volumes of four additional standards were prepared to concentrations of 250, 25, 2.5, and 0.25 μg/ml, respectively. A negative standard comprising 10 ml of DMSO containing no diphenylhydantoin was also used.

B. Apparatus

Fluorescence was measured with an Aminco-Bowman Spectrophotofluorometer (American Instrument Co., Silver Spring, Md., U.S.A.). Excitation and emission wavelengths were set at 400 and 453 nm, respectively. Reaction rates were monitored on a strip-chart recorder connected to the fluorometer. Reaction rates are presented herein as the change in strip-chart units (fluorescence units) per minute. All fluorescence measurements were conducted at 25° C.

C. Assay Procedure 3.0 ml aliquots of a reagent were prepared in 50 mM Bicine buffer (pH 8.2) in a cuvette to contain 0.0157 units/ml of β-galactosidase and an amount of antiserum sufficient to decrease the reaction rate to about 15% of that observed in the absence of antibody. To separate aliquots of the reagent were added 10 μl of the various standard diphenylhydantoin solutions. After mixing, 10 μl of a 12 μM aqueous solution of the N[1]-labeled conjugate (prepared as described in 1-I above) in 0.2% (volume:volume) Tween-20 surfactant (a polyoxyethylene derivative of fatty acid partial esters of sorbitol anhydride from J. T. Baker, Phillipsburg, N.J., USA) was added to each cuvette and the rate of increase of fluorescence monitored for 2 to 3 minutes. A control was also run following the same procedure except that the initial reagent contained no antiserum.

D. Results

The response to the various standards was expressed for each cuvette as percent of competition defined as:

$$\text{percent of competition} = \frac{\text{rate (standard measured)} - \text{rate (negative standard)}}{\text{rate (control)} - \text{rate (negative standard)}}$$

The results are given in the following table:

| diphenylhydantoin concentration in standard (μg/ml) | percent of competition |
|---|---|
| 2500 | 84.2 |
| 250 | 61.3 |
| 25 | 32.9 |
| 2.5 | 9.3 |
| 0.25 | 2.0 |

The results demonstrate that the labeled conjugate and the antiserum prepared using the immunogen conjugate are useful in an assay for diphenylhydantoin.

2. N³-Derivatives

2-I. PREPARATION OF THE LABELED CONJUGATE

The N³-conjugated β-galaactosyl-umbelliferone-diphenylhydantoin labeled compounds are prepared according to the reaction scheme shown in Table 3. This synthetic route is exemplified by the following method of preparing N-[4-(5,5-diphenylhydantoinyl-3)-butyl]-7-β-galactosylcoumarin-3-carboxamide (12). To follow this synthesis in Table 3, n equals 4.

3-(4-Aminobutyl)-5,5-diphenylhydantoin (10).

A mixture of 9 g (0.025 mol) of 3-(4-carboxybutyl)-5,5-diphenylhydantoin (9) [Cook et al, *Res. Comm. in Chem. Path. Pharmacol.* 5:767(1973)], 3.6 ml of triethylamine, and 70 ml of dry DMF were cooled to −5° C. while stirring under argon. To this mixture was added 2.77 g (0.025 mol) of ethyl chloroformate. After 90 minutes the reaction was filtered to remove precipitated triethylamine hydrochloride. An additional 100 ml of DMF was added and the temperature of the solution adjusted to 5° C. A solution of 5.1 g (0.078 mol) of sodium azide in 40 ml of $H_2O$ was added at such a rate as to keep the temperature between 5° and 7° C. After 2 hours stirring at this temperature, the reaction was diluted with 1.2 liters of $H_2O$ and extracted with seven 300 ml portions of 1:1 (v:v) ether:pentane. The combined organic extracts were dried over anhydrous magnesium sulfate, filtered and evaporated to give 6.5 g of a gummy residue which was taken up in 150 ml of absolute ethanol and refluxed for 4 hours.

Evaporation of the ethanol gave an oil that was dissolved in 100 ml of dioxane and 100 ml of 6 N hydrochloric acid and refluxed overnight. When cool, the reaction mixture was evaporated to dryness. The residue was crystallized from ethanol to give 1.8 g of the hydrochloride salt of the amino-hydantoin (10) as a white solid, mp 282°–285° C. (decomp.).

Analysis: Calculated for $C_{19}H_{21}N_3O_2 \cdot HCl$: C, 63.41; H, 6.16; N, 11.68. Found: C, 62.62; H, 6.15; N, 11.31.

Mass spectrum (70 eV) m/e: 324 [MH+], 293 [M+ minus $CH_2NH_2$].

The hydrochloride salt was dissolved in 50 ml of $H_2O$ and neutralized with solid sodium bicarbonate. THe free base precipitated and was recrystallized from ethanol to give 1.1 g of the amino-hydantoin (10) as a white solid, mp 137°–138° C.

Analysis: Calculated for $C_{19}H_{21}N_3O_2$: C, 70.59; H, 6.55; N, 13.00. Found: C, 70.08; H, 6.50; N, 12.55.

N-[4-(5,5-Diphenylhydantoinyl-3)-butyl]-7-β-galactosylcoumarin-3-carboxamide (12).

In a 500 ml flask was placed a solution containing 24 g of potassium hydroxide dissolved in 80 ml of $H_2O$ and 240 ml of methanol. The solution was cooled to 5° C. and stirred while 20 g (0.035 mols) of ethyl-7-β-galactosylcoumarin-3-carboxylate [Burd et al, *Clin. Chem.* 23:1402 (1977)] was added in one portion. After stirring for 5 minutes, the reaction was heated for 15 hours at 50° C. When cool, the methanol was removed under reduced pressure. The concentrated aqueous solution was acidified to pH 2.0 with concentrated hydrochloric acid. The white precipitate was collected, washed with cold $H_2O$ and recrystallized from hot $H_2O$. The crystals were washed with acetone and dried at 80° C. for 1 hour. This gave 12 g of 7-β-galactosylcoumarin-3-carboxylic acid as white crystals, mp 250°–255° C.

Analysis: Calculated for $C_{16}H_{16}O_{10}$: C, 52.17; H, 4.38. Found: C, 52.31; H, 4.63.

A mixture of 737 mg (2.0 mmol) of 7-β-galactosyl-coumarin-3-carboxylic acid, 20 ml of dry DMF, and 0.278 ml (202 mg, 2 mmol) of triethylamine was placed in a 3-necked, 50 ml round bottom flask fitted with a stirrer, argon inlet-outlet, and thermometer. When the acid had all dissolved, the contents of the flask were cooled to −10° C. and 273 mg (2 mmol) of isobutyl chloroformate was added. After 10 minutes, 808 mg (2.5 mmol) of 3-(4-aminobutyl)-5,5-diphenylhydantoin (10) and an additional 0.278 ml of triethylamine was added

TABLE 3

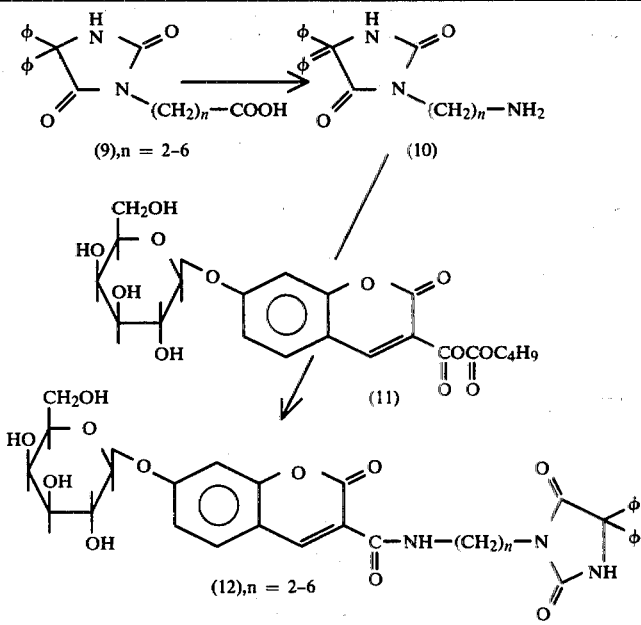

for reaction with the formed mixed anhydride (11). Thirty minutes later the reaction was allowed to warm to room temperature and stirred for one hour.

Silica gel 60, 7 g, was added to the reaction mixture and the solvent evaporated under high vacuum. The impregnated silica gel was placed atop a column of 200 g of silica gel 60 made up in ethyl acetate. The column was eluted with a gradient of 2 liters of ethyl acetate to 2 liters of 1:1 (v:v) ethyl acetate:ethanol. Fifteen ml fractions were collected. Fractions 128 to 175 were combined and evaporated to give a gummy solid. Recrystallization from ethanol gave 550 mg of the labeled conjugate (12) as fine white crystals, mp 145° C.

Analysis: Calculated for $C_{35}H_{35}N_3O_{11}$: C, 62.40; H, 5.24; N, 6.24. Found: C, 61.72; H, 5.30; N, 6.21.

Mass Spectrum (17 ma) m/e: 674 [MH+], 512 [MH+ minus $C_6H_{10}O_5$]. $[\alpha]_D = -30.48°$ (c 1.0, methanol).

The above-described synthesis of the $N^3$-labeled conjugate (12), n=4, can be modified to yield labeled conjugates wherein n=2 through 6 by replacing the starting material 3-(4-carboxybutyl)-5,5-diphenylhydantoin (9) in the synthesis of the amino-hydantoin (10) with the appropriate 3-($\omega$-carboxyalkyl)-5,5-diphenylhydantoin as follows:

| n | alkylene |
|---|----------|
| 2 | ethylene |
| 3 | propylene |
| 5 | pentylene |
| 6 | hexylene |

2-II. PREPARATION OF THE IMMUNOGEN CONJUGATE 24.3 mg (75 μmol) of 3-(4-carboxybutyl)-5,5-diphenylhydantoin was dissolved in 0.75 ml dioxane. The solution was cooled to 5° to 10° C. in an ice water bath and 17.5 μl (8.15 mg. 75 μmol) of ethyl chloroformate was added. The solution was allowed to react for 15 minutes at 5° to 10° C. before adding it to the protein solution. The protein solution was prepared by dissolving 125 mg (2.08 μmol) of bovine serum albumin (BSA) in 3.25 ml $H_2O$ containing 125 μl of 1 N sodium hydroxide. While vortex mixing, 3.25 ml dioxane was slowly added to the alkaline BSA solution. The BSA solution was placed in an ice bath and the activated diphenylhydantoin derivative added. The solution was mixed and allowed to react for 2 hours.

The reaction mixture was brought to room temperature and chromatographed with 50 mM Tris buffer [tris(hydroxymethyl) aminomethane], pH 8.2, through a column of G-25 Sephadex (2.5×50 cm). The ultraviolet absorbance of the 12 ml fractions was monitored and the immunogen conjugate eluting in the column void volume (fractions 7 to 10) was pooled. The unreacted diphenylhydantoin derivative eluted in fractions 15 to 20. Analysis of the absorption spectrum of the diphenylhydantoin-BSA conjugate indicated 28 moles of diphenylhydantoin derivative per mole of BSA.

2-III. BINDING ASSAY FOR DIPHENYLHYDANTOIN

A. Reagents and Apparatus

The reagents and apparatus were the same as those used in the assay employing the $N^1$-derivatives described in 1-III above except that the antiserum was obtained by immunizing rabbits with the $N^3$-conjugated immunogen prepared according to 2-II above.

B. Assay Procedure

The procedure was the same as that used in the assay employing the $N^1$-derivatives described in 1-III above except that the solutions of labeled conjugate used were 10 μl aliquots of an 8 μM aqueous solution of the $N^3$-labeled conjugate (prepared as described in 2-I above) in 0.2% (volume:volume) Tween-20 surfactant.

C. Results

The results, expressed as described in 1-III above, are given in the following table:

| diphenylhydantoin concentration in standard (μg/ml) | percent of competition |
|---|---|
| 2500 | 68.9 |
| 250 | 60.0 |
| 25 | 47.2 |
| 2.5 | 23.2 |
| 0.25 | 1.1 |

The results demonstrate that the labeled conjugate and the antiserum prepared using the immunogen conjugate are useful in an assay for diphenylhydantoin.

3. o-Phenyl Derivatives

3-III. PREPARATION OF THE LABELED CONJUGATE

The o-phenyl-conjugated β-galactosyl-umbelliferone-diphenylhydantoin labeled compounds are prepared according to the reaction scheme shown in Table 4. This synthetic route is exemplified by the following method for preparing N-{4-[2-(5-phenylhydantoinyl-5)-phenoxy]-butyl}-7-β-galactosylcoumarin-3-carboxamide (16). To follow this synthesis in Table 4, n equals 4.

2-[4-(N-Phthalimido)-butoxy]-benzophenone (13).

In a 1 liter, 3-neck round bottom flask was placed 8.64 g of a 50% suspension of sodium hydride (NaH) in mineral oil (0.18 mol). The NaH was washed free of mineral oil with hexane under an argon atmosphere. The washed NaH was then suspended in 350 ml of dry dimethylformamide (DMF) and stirred while a solution of 34.4 g (0.173 mol) of 2-hydroxybenzophenone in 40 ml of DMF was added over a 1 hour period. Thirty minutes after the addition was complete, 52 g (0.184 mol) of N-(4-bromobutyl)-phthalimide in 150 ml of dry DMF was added over a 20 minute period. After stirring at room temperature for 18 hours, the reaction was diluted with 200 ml of water ($H_2O$) and the precipitate collected and dried to yield 49 g of the benzophenone (13), mp 119°–121° C. A 1 g sample was recrystallized from ethanol to give 740 mg of white needles, mp 121°–122° C.

Analysis: Calculated for $C_{25}H_{21}NO_4$: C, 75.17; H, 5.30; N, 3.51. Found: C, 74.78; H, 5.26; N, 3.79.

NMR Spectrum (CDCl$_3$): δ 1.5 (m, 4H), 3.5 (m, 2H), 3.9 (m, 2H).

TABLE 4

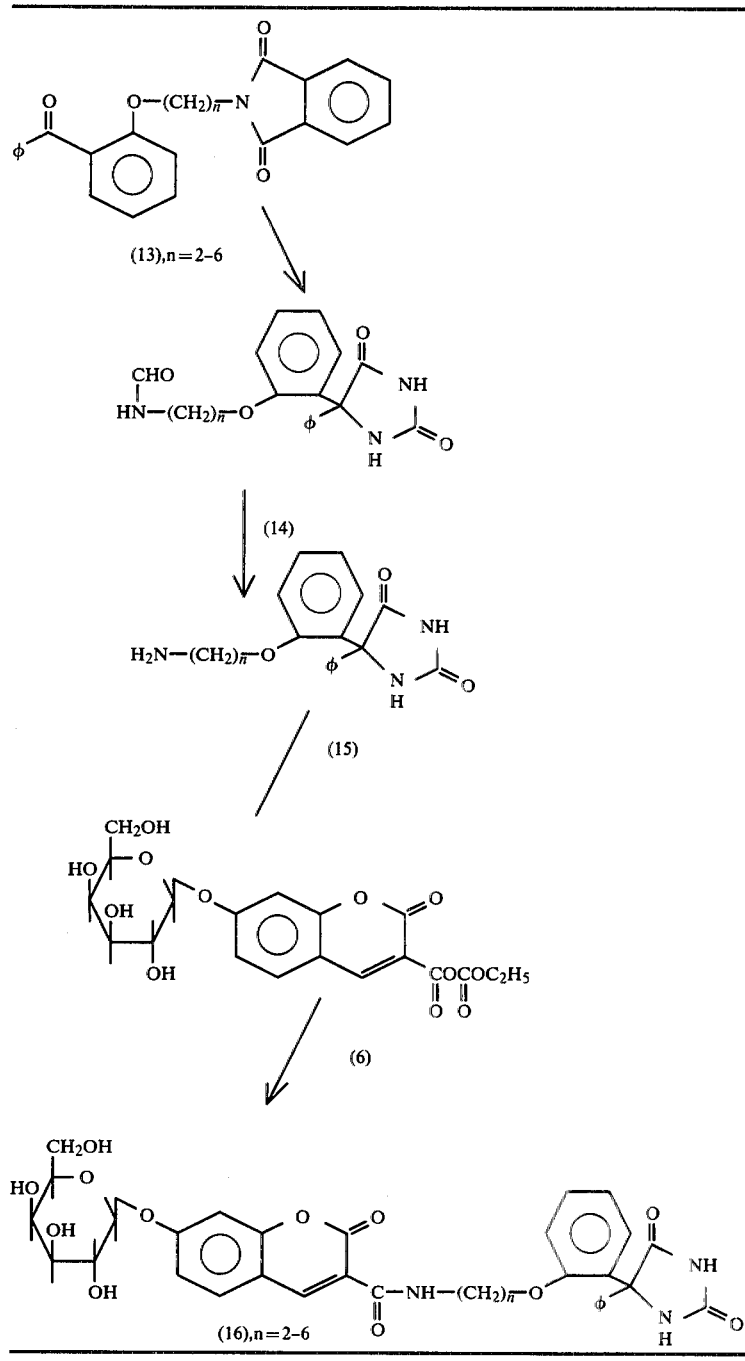

5-[2-(4-N-Formylaminobutoxy)-phenyl]-5-phenyl-hydantoin (14).

A mixture of 22.4 g (0.056 mol) of 2-[4-(N-phthalimido)-butoxy]-benzophenone (13), 4.15 g (0.064 mol) of potassium cyanide, 17.3 g (0.18 mol) of ammonium carbonate, 24 ml of $H_2O$, and 200 ml of DMF was placed in a steel autoclave and heated at 110° C. for 4 days. The contents were cooled and adsorbed onto 100 g of silica gel 60 and placed atop a 700 g column of silica gel made up in 9:1 (v:v) carbon tetrachloride:acetone. Elution was with the same solvent and fractions of approximately 20 ml volumes were collected. Fractions 276 to 803 were combined and evaporated to give 4.65 g of solid. Recrystallization from ethanol gave 2.65 of the hydantoin (14) as a white solid, mp 201°-203° C.

Analysis: Calculated for $C_{20}H_{21}N_3O_4$: C, 65.38; H, 5.76; N, 11.44. Found: C, 65.23; H, 5.79; N, 11.47.

NMR Spectrum (NaOD-$D_2O$): $\delta$ 1.2 (m, 4H), 3.0 (m, 2H), 3.2 to 4.0 (m, 2H).

5-[2-(4-Aminobutoxy)-phenyl]-5-phenylhydantoin (15).

A solution of 3.5 g (9.4 mmol) of 5-[2-(4-N-formylamino-butoxy)-phenyl]-5-phenylhydantoin (14) in 100 ml of 1 N sodium hydroxide was heated on the steam bath for 24 hours. The solution was cooled and neutralized with carbon dioxide until precipitation ceased. The precipitate was filtered and recrystallized twice; first from pyridine-2-propanol, then from methanol to give 1.5 g of the aminohydantoin (15) as fine white crystals, mp 235° C. (decomposed).

Analysis: Calculated for $C_{19}H_{21}N_3O_3$: C, 67.24; H, 6.24; N, 12.38. Found: C, 67.56; H, 6.29; N, 12.56.

NMR Spectrum (NaOD-$D_2O$): δ 0.9 (m, 4H), 2.2 (m, 2H), 3.2 (m, 2H).

N-{4-[2-(5-Phenylhydantoinyl-5)-phenoxy]-butyl}-7-β-galactosylcoumarin-3-carboxamide (16).

A mixture of 808 mg (2 mmol) of the potassium salt of 7-β-galactosylcoumarin-3-carboxylic acid [Burd et al, al, Chem. 23:1402(1977)] and 20 ml of dry DMF was cooled to 0° C. To this mixture was added 216 mg (2 mmol) of ethyl chloroformate and the reaction stirred for one hour at this temperature to form the mixed anhydride (6). Then 638 mg (2 mmol) of 5-[2-(4-aminobutoxy)-phenyl]-5-phenylhydantoin (15), 244 mg of 4-dimethylaminopyridine, and 5 ml of dry pyridine were added. After stirring for 5 hours, the reaction was stored overnight at 0° C., then adsorbed onto 7 g of silica gel 60. The impregnated silica gel was placed atop a column of 200 g of silica gel 60 and the column eluted with a gradient of 2 liters of ethyl acetate to 2 liters of 1:1 (v:v) ethyl acetate:ethanol. Ten ml fractions were collected. Fractions 143 to 160 were combined to give approximately 200 mg of the labeled conjugate (16) as a glassy solid.

The solid was taken up in methanol and chromatographed on Sephadex LH-20 (45 cm by 3.2 cm, Pharmacia Fine Chemicals), eluting with methanol. Seven ml fractions were collected. Fractions 30 to 40 were combined and evaporated to give 100 mg of the desired labeled conjugate (16) as a pale, glassy solid.

Analysis: Calculated for $C_{35}H_{35}N_3O_{12}.H_2O$: C, 59.40; H, 5.27; N, 5.94. Found: C, 59.51; H, 5.04; N, 6.14.

$[α]_D = -39.04°$ (c 1.0, methanol).

The above-described synthesis of the o-phenyl-labeled conjugate (16), n=4, can be modified to yield labeled conjugates wherein n=2 through 6 by replacing the starting material N-(4-bromobutyl)-phthalimide in the synthesis of the phthalimide (13) with the appropriate N-(ω-bromoalkyl)-phthalimide as follows:

| n | alkylene |
|---|---|
| 2 | ethylene |
| 3 | propylene |
| 5 | pentylene |
| 6 | hexylene |

3-II. PREPARATION OF THE IMMUNOGEN CONJUGATE

This synthesis is shown schematically in Table 5 and is exemplified for n=4 as follows:

TABLE 5

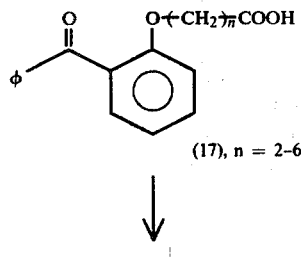

(17), n = 2-6

↓

TABLE 5-continued

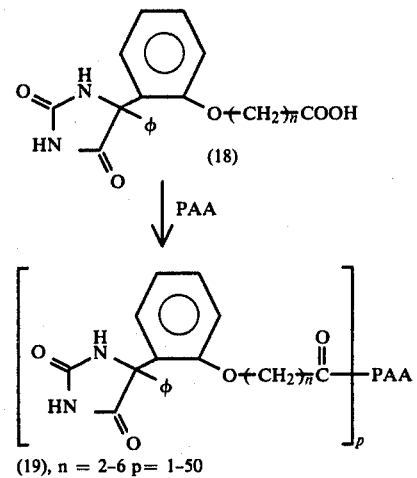

(19), n = 2-6 p= 1-50

A mixture of 2.52 g (0.11 gram-atom) of sodium and 400 ml of absolute ethanol was stirred until all of the sodium dissolved. To this was added 19.8 g (0.1 mol) of 2-hydroxybenzophenone. After 45 minutes the deep yellow solution was combined with 20.9 g (0.1 mol) of ethyl-5-bromovalerate. The reaction was refluxed for 44 hours, then cooled and diluted with 250 ml of 1 N sodium hydroxide and 250 ml of ether. The ether layer was separated and the aqueous phase saturated with sodium chloride, then extracted with four 200 ml portions of ether. The ether extracts were combined, dried over anhydrous magnesium sulfate, filtered, and evaporated to give 40 g of a yellow oil of 2-(4-carbethoxybutoxy)-benzophenone (17).

This ester was not characterized but instead was hydrolyzed by refluxing it 15 hours in a mixture of 500 ml of dioxane and 60 ml of concentrated hydrochloric acid. Evaporation gave a brown oil that was partitioned between 200 ml of ether and 200 ml of saturated sodium bicarbonate solution. The layers were separated and the ether phase extracted with a second 200 ml portion of sodium bicarbonate solution. The bicarbonate extracts were combined, acidified with hydrochloric acid, and extracted with three 200 ml portions of ether. The combined ether extracts were evaporated to give 23 g of a brown oil that was chromatographed on 2000 g of silica gel 60 eluting with 19:1 (v:v) carbon tetrachloride:acetone. Twenty ml fractions were collected. Fractions 1271 to 1670 were combined and evaporated to give 11.1 g of the benzophenone (17). Two recrystallizations from methylene chloride gave white crystals, mp 80°-81° C.

Analysis: Calculated for $C_{18}H_{18}O_4$: C, 72.46; H, 6.09. Found: C, 72.29; H, 6.07.

A mixture of 17.8 g (0.06 mol) of 2-(4-carboxybutoxy)-benzophenone (17), 4.15 g (0.064 mol) of potassium cyanide, 17.3 g (0.18 mol) of ammonium carbonate, 24 ml of $H_2O$, and 200 ml of DMF was placed in a steel autoclave and heated to 110° C. for 5 days. The autoclave was cooled and the contents dissolved in 800 ml of 10% aqueous sodium hydroxide solution. It was washed with two 400 ml portions of ether and acidified to pH 4.5 with 6 N hydrochloric acid. A precipitate occurred that was filtered and dried to give 24.6 g of 5-[2-(4-carboxybutoxy)-phenyl]-5-phenylhydantoin (18). Two recrystallizations from aqueous methanol gave a white solid, mp 231°–232° C.

Analysis: Calculated for $C_{20}H_{20}N_2O_5$: C, 65.20; H, 5.48; N, 7.61. Found: C, 64.92; H, 5.62; N, 7.90.

NMR Spectrum ($C_5D_5N$): δ 1.2 (m, 2H), 1.6 to 2.0 (m, 4H), 3.2 (m, 2H).

27.6 mg (74 μmol) of the acid (18) was suspended in 1.5 ml dioxane. The solution was cooled to 5° to 10° C. in an ice water bath and 17.5 μl (14.5 mg, 75 μmol) of tri-N-butylamine added. After mixing, 6 μl (8.15 mg, 75 μmol) of ethyl chloroformate was added and mixed. The solution was allowed to react for 15 minutes at 5° to 10° C. before adding it to the protein solution. The protein solution was prepared by dissolving 125 mg (2.08 μmol) of bovine serum albumin (BSA, represented in Table 5 as PAA) in 3.25 ml $H_2O$ containing 125 μl of 1 N sodium hydroxide. While vortex mixing, 3.25 ml dioxane was slowly added to the alkaline BSA solution. The BSA solution was then placed in an ice bath and the activated diphenylhydantoin derivative added. 0.5 ml of water was added 2 minutes after the activated diphenylhydantoin derivative in order to keep the BSA in solution.

After 1.75 hours, the reaction mixture was brought to room temperature and chromatographed with 50 mM Tris buffer, pH 8.2, through a 2.8×42 cm column of G-25 Sephadex (Pharmacia Fine Chemicals). Fractions of 5.1 ml were collected and the absorbance at 280 nm monitored. The immunogen conjugate (19) eluted in the void volume and these fractions (13 to 19) were pooled. The unreacted diphenylhydantoin eluted in fractions 35 to 47. Analysis of the absorbance of the immunogen conjugate indicated 8.1 moles of diphenylhydantoin per mole of BSA.

The above-described synthesis of the o-phenyl-immunogen conjugate (19), n=4, can be modified to yield conjugates wherein n=2 through 6 by replacing ethyl-5-bromovalerate in the described synthesis of the benzophenone (17) as follows:

| n | starting material |
|---|---|
| 2 | ethyl-3-bromopropionate |
| 3 | ethyl-4-bromobutyrate |
| 5 | ethyl-6-bromocaproate |
| 6 | ethyl-7-bromoheptanoate |

3-III. BINDING ASSAY FOR DIPHENYLHYDANTOIN

A. Reagents and Apparatus

The reagents and apparatus were the same as those used in the assay employing the $N^1$-derivatives described in 1-III above except that the antiserum was obtained by immunizing rabbits with the o-phenyl-conjugated immunogen prepared according to 3-II above and that the diphenylhydantoin standards used were prepared at concentrations of 0, 5, 10, 20, and 30 μg/ml in serum.

B. Assay Procedure 3.0 ml aliquots of a reagent were prepared in 50 mM Bicine buffer [pH 8.2; N,N-bis-(2-hydroxyethyl)-glycine] in a cuvette to contain 0.018 units/ml of β-galactosidase and an amount of antiserum sufficient to decrease the reaction rate to about 10% of that observed in the absence of antibody in the final reaction. To separate aliquots of the reagent were added 100 μl of the various standard diphenylhydantoin sera diluted 1:50 in 0.5% Tween 20 followed by 100 μl of a 1.05 μM aqueous solution of the o-phenyl-labeled conjugate (prepared as described in 3-I above). After mixing, the reaction mixtures were incubated 20 minutes at 25° C. and the fluorescence measured for each cuvette.

C. Results

The results, expressed in terms of fluorescence units read from the instrument, are given in the following table:

| diphenylhydantoin concentration in standard (μg/ml) | fluorescence units |
|---|---|
| 0 | 72 |
| 5 | 304 |
| 10 | 425 |
| 20 | 595 |
| 30 | 757 |

The results demonstrate that the labeled conjugate and the antiserum prepared using the immunogen conjugate are useful in an assay for diphenylhydantoin.

What is claimed is:

1. A β-galactosyl-umbelliferone-diphenylhydantoin conjugate of the formula:

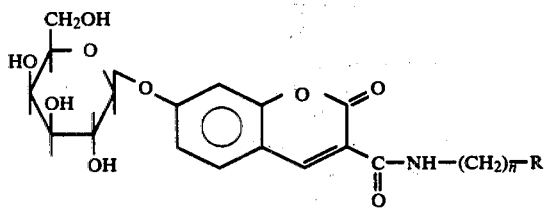

wherein
n=2 through 6;

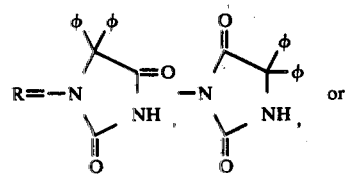 or

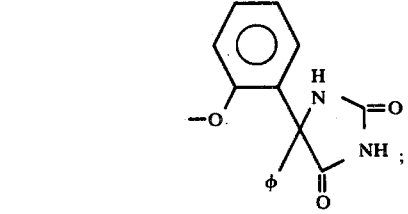

φ=phenyl.

2. The conjugate of claim 1 wherein n=4.

3. N-[4-(5,5-Diphenylhydantoinyl-1)-butyl]-7-β-galactosylcoumarin-3-carboxamide.

4. N-[4-(5,5-Diphenylhydantoinyl-3)-butyl]-7-β-galactosylcoumarin-3-carboxamide.

5. N-{4-[2-(5-Phenylhydantoinyl-5)-phenoxy]-butyl}-7-β-galactosylcoumarin-3-carboxamide.

* * * * *